United States Patent [19]

Ascione et al.

[11] Patent Number: 5,783,172
[45] Date of Patent: Jul. 21, 1998

[54] DENTIFRICE COMPOSITIONS COMPRISING AN ABRASIVE SYSTEM AND A SURFACTANT SYSTEM

[75] Inventors: Jean-Marc Ascione, Paris; Pascal Sterle, Soisy S/Montmorency, both of France

[73] Assignee: L'Oreal, France

[21] Appl. No.: 569,614

[22] Filed: Dec. 8, 1995

[30] Foreign Application Priority Data

Dec. 9, 1994 [FR] France .................. 94 14862

[51] Int. Cl.$^6$ .................. A61K 33/24; A61K 7/16; A61K 31/08
[52] U.S. Cl. .................. 424/49; 424/717; 514/723
[58] Field of Search .................. 424/49, 717; 514/723

[56] References Cited

U.S. PATENT DOCUMENTS

| | | | |
|---|---|---|---|
| 3,821,372 | 6/1974 | Vanlerberghe et al. | 424/170 |
| 3,928,224 | 12/1975 | Vanlerberghe et al. | 252/172 |
| 3,966,398 | 6/1976 | Vanlerberghe et al. | 8/11 |
| 4,087,466 | 5/1978 | Vanlerberghe et al. | 260/615 B |
| 4,307,079 | 12/1981 | Zorayan et al. | 424/70 |
| 4,515,775 | 5/1985 | Vanlerberghe et al. | 424/70 |
| 4,828,824 | 5/1989 | Grollier | 424/52 |
| 4,837,008 | 6/1989 | Rudy et al. | 424/53 |
| 5,037,633 | 8/1991 | Ziemkiewicz et al. | 424/49 |

FOREIGN PATENT DOCUMENTS

| | | |
|---|---|---|
| 1 477 048 | 4/1966 | France . |
| 2 574 786 | 6/1966 | France . |
| 2 091 516 | 1/1972 | France . |
| 2 169 787 | 9/1973 | France . |
| 2 328 763 | 5/1977 | France . |
| 2 603 800 | 3/1988 | France . |
| 1155712 | 4/1966 | United Kingdom . |
| 1155713 | 4/1966 | United Kingdom . |
| 1246929 | 9/1971 | United Kingdom . |

*Primary Examiner*—Phyllis G. Spivack
*Attorney, Agent, or Firm*—Finnegan, Henderson, Farabow, Garrett & Dunner, L.L.P.

[57] ABSTRACT

Compositions comprising, in an aqueous vehicle, an abrasive system containing an alkali metal bicarbonate and a surfactant system, where the surfactant system comprises a non-ionic poly(hydroxypropyl ether) surfactant. Such compositions are particularly useful as oral hygiene compositions.

These compositions may be used as, or for the manufacture of, a dentifrice in the form of a paste, a gel, a liquid or a chewing gum.

12 Claims, 3 Drawing Sheets

DENTIFRICE COMPOSITIONS COMPRISING AN ABRASIVE SYSTEM AND A SURFACTANT SYSTEM

The present invention relates to new compositions comprising, in an aqueous vehicle, an abrasive system containing at least one alkali metal bicarbonate and a surfactant system containing at least one non-ionic poly (hydroxypropyl ether) surfactant, these compositions being represented in particular by compositions for oral hygiene.

The invention also relates to the use of these compositions as, or for manufacture of, a dentifrice in the form of a paste, a gel, a liquid or a chewing gum.

Use is commonly made, in the field of oral hygiene, of alkali metal bicarbonates, in particular for neutralizing the acids responsible for caries and especially for their abrasiveness.

Moreover, in order to formulate so-called "aqueous" dentifrices, thus described because they contain at least 3% by weight of water, use has until now been made of surface-active agents of anionic type, the role of which is to introduce both a satisfactory foaming power and a satisfactory detergent power. Mention may more particularly be made, among the latter, of sodium lauryl sulphate, which is indeed the most commonly employed.

Now, the inventors have observed that, in these formulations, the alkali metal bicarbonates, initially introduced in the form of solid particles (powders), are partially dissolved. This partial dissolution brings about a significant loss in the abrasive power associated with the final composition. In order to overcome this disadvantage, the inventors have carried out a great deal of research into the matter and have discovered, surprisingly, that a much lower solubilization of the alkali metal bicarbonate could be obtained in aqueous compositions comprising a non-ionic surfactant system of the poly(hydroxypropyl ether) type, compared to the degree of solubilization in aqueous compositions comprising a sodium lauryl sulphate.

Thus, using equal amounts of bicarbonates, the abrasive power of the compositions in accordance with the invention is markedly greater than that of the compositions of the prior art. In addition, the surfactant system selected according to the invention has an excellent foaming and detergent power.

These discoveries are the basis of the present invention.

The subject of the present invention is therefore new compositions of the type comprising, in an aqueous vehicle, an abrasive system containing at least one alkali metal bicarbonate and a surfactant system, which are characterized in that the said surfactant system comprises at least one non-ionic poly(hydroxypropyl ether) surfactant.

Another subject of the present invention is compositions of this type for oral use, in particular dentifrices.

The present invention is also targeted at the use of these compositions as, or for the manufacture of, a dentifrice which can be in the form of a paste, a gel, a liquid or a chewing gum.

However, other characteristics, aspects, subjects and advantages of the invention will become still more clearly apparent on reading the description and the examples which follow.

The alkali metal bicarbonate which can be used according to the invention is preferably chosen from sodium bicarbonate or potassium bicarbonate.

The surfactants of poly(hydroxypropyl ether) type are products which are already known per se. Preferably, according to the present invention, the non-ionic poly(hydroxypropyl ether) surfactant(s) are chosen from the compounds of following structures:

(A) The compounds corresponding to the formula (I):

$$RO + C_3H_5(OH)O +_n - H \quad (I)$$

in which the $-(C_3H_5(OH)O)-$ group is identical or different and represents the following structures (I.a), (I.b) and (I.c):

$$+CH_2-CHOH-CH_2-O+ \quad (I.a)$$

$$\begin{array}{c} +CH_2-CHO+ \\ | \\ CH_2OH \end{array} \quad (I.b)$$

$$\begin{array}{c} +CH-CH_2-O+ \\ | \\ CH_2OH \end{array} \quad (I.d)$$

and R and n have, together, one of the meanings a), b), or c) below:

a) R denotes a $C_{10}-C_{14}$ alkyl radical or a mixture of $C_{10}-C_{14}$ alkyl radicals, and n is a whole or decimal number varying from 2 to 10 and preferably from 3 to 6.

b) R denotes a group of formula (II):

$$R_2-CONH-CH_2-CH_2-O-CH_2-CH_2- \quad (II),$$

in which $R_2$ denotes a $C_{11}-C_{17}$ -alkyl or -alkenyl radical or a mixture of $C_{11}-C_{17}$ -alkyl and/or -alkenyl radicals, and n denotes a whole or decimal number varying from 1 to 5 and preferably from 1.5 to 4.

c) R denotes a group of formula (III):

$$R_3-CHOH-CH_2- \quad (III),$$

in which $R_3$ denotes a $C_7-C_{21}$ -aliphatic, -cycloaliphatic or -arylaliphatic radical, or a mixture thereof, the aliphatic chains denoting in particular alkyl chains which can contain from 1 to 6 ether, thioether and/or hydroxymethylene groups, and n denotes a whole or decimal number varying from 1 to 10.

These surfactants of formula (I) can be prepared according to the processes described in French patent documents 1,477,048, 2,328,763 and 2,091,516, the disclosures of which are hereby incorporated by reference.

(B) The non-ionic poly(hydroxypropyl ether) compounds prepared by condensation, in acid catalysis, and at a temperature ranging from 50° to 120° C., of 2 to 10 mol, preferably, 2.5 to 6 mol, of glycidol per mole of alcohol containing 10 to 14 carbon atoms or of alpha-diol containing 10 to 14 carbon atoms, the glycidol being slowly added to the alcohol or to the alpha-diol.

The process for the preparation of these compounds is described in French patent document 2,169,787, the disclosure of which is hereby incorporated by reference.

(C) The non-ionic poly(hydroxypropyl ether) compounds prepared by polyaddition of glycerol monochlorohydrin to a polyhydroxylated organic compound in the presence of a strong base, with removal of the water, by distillation, as it is formed. A base is considered strong at a pH greater than 10.

These compounds are described in French patent document 2,574,786, the disclosure of which is hereby incorporated by reference.

The more particularly preferred compounds according to the invention, among the non-ionic poly(hydroxypropyl ether) surfactants described in paragraphs (A), (B) and (C) above, are:

i) those of following formulae (IV) and (V):

in which formula (V) $R_1$ denotes a mixture of $C_{10}H_{21}$ and $C_{12}H_{25}$ alkyl radicals, 2i) the non-ionic poly(hydroxypropyl ether) compounds prepared by condensation, in alkaline catalysis, of 3.5 mol of glycidol with an alpha-diol having 12 carbon atoms, according to the process described in French Patent FR 2,091,516, 3i) the compounds of formula (VI):

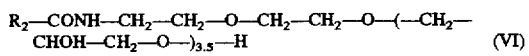

in which $R_2$ denotes a mixture of radicals comprising the following alkyl and alkenyl radicals: $C_{11}H_{23}$, $C_{13}H_{27}$, the radicals derived from coconut fatty acids and the radical derived from oleic acid, 4i) the compounds prepared by condensation of 3.5 mol of glycidol with a mixture of $C_{11}$–$C_{14}$ alpha-diols described in French patent document 2,091,516.

Dodecanediol polyglycerolated with 3.5 mol of glycerol is more particularly preferred.

According to a preferred embodiment of the compositions according to the invention, the surfactant system contains only non-ionic surfactant(s) in accordance with the invention.

In the compositions according to the invention, the at least one alkali metal bicarbonate is generally present in concentrations by weight of from approximately 0.5 to 80% and preferably from approximately 1 to 50%, and the at least one non-ionic poly(hydroxypropyl ether) surfactant is generally present in concentrations by weight of from approximately 0.1 to 10% and preferably from approximately 0.2 to 5% with respect to the total weight of the composition.

The compositions in accordance with the invention which are intended for oral hygiene can contain, in addition to the alkali metal bicarbonate and the non-ionic poly (hydroxypropyl ether) surfactant, either as a vehicle or for their own activity, excipients or ingredients commonly used in products for oral use.

The compositions in accordance with the invention are prepared according to the usual processes corresponding to the vehicles chosen. The physiologically acceptable vehicle can be different in nature according to the form chosen for the composition: optionally thickened aqueous or aqueous/ alcoholic medium, pasty or solid excipient, gum, and the like.

Depending upon the desired forms, these compositions can also contain other abrasive agents, among which mention may be made of, for example, silica, alumina, calcium hydrogenphosphate and calcium carbonate, anticarious agents such as, for example, sodium or potassium or amine fluorides or sodium monofluorophosphate, antibacterial agents such as, for example, chlorhexidine, alexidine, hexetidine, cetylpyridinium chloride or 2,4,4'-trichloro-2'- hydroxydiphenyl ether, antiinflamnmatory agents, antihalitosis agents, enzymes, vitamins, trace elements, haemostatic agents, healing agents and agents which are active on the gum. Moreover, they can contain other usual agents such as binding agents, sweeteners, humectants or fresheners, preservatives, dyes, fragrances, flavouring agents, peptizing agents and plasticizers.

Concrete, but in no way limiting, examples illustrating the invention will now be given.

EXAMPLE 1

The preservation of the sodium bicarbonate crystals in aqueous solutions containing 2% of non-ionic poly (hydroxypropyl ether) surfactant and the dissolution of the same crystals in solutions containing 2% of sodium lauryl sulphate were studied, at different concentrations, by direct observation of the said solutions with an optical microscope.

To do this, the six compositions below (% by weight) were prepared and were then brought, with stirring, to a temperature of 40° C., in order to obtain solutions. These solutions were then allowed to return to a temperature of 20° C. and they were observed with a microscope.

| Solution | 11% NaHCO$_3$ | 12% NaHCO$_3$ | 13% NaHCO$_3$ | 2% Non-ionic surfactant* | 2% Na lauryl sulphate |
|---|---|---|---|---|---|
| S1 | X | | | X | |
| S2 | X | | | | X |
| S3 | | X | | X | |
| S4 | | X | | | X |
| S5 | | | X | X | |
| S6 | | | X | | X | dodecanediol polyglycerolated with 3.5 mol of glycerol, prepared according to the process described in French patent document 2,091,516.

The photographs of these observations are attached and labelled FIGS. 1–6. FIGS. 1 to 6 correspond to the photographed solutions 1 to 6 respectively. In these photographs, the crystalline network which appears at the bottom of the solutions S2, S4 and S6 was identified as being a sodium lauryl sulphate network.

BRIEF DESCRIPTION OF THE FIGURES

The file of this patent contains at least one drawing executed in color. Copies of this patent with color drawing (s) will be provided by the Patent and Trademark Office upon request and payment of the necessory fee.

Figure 1:
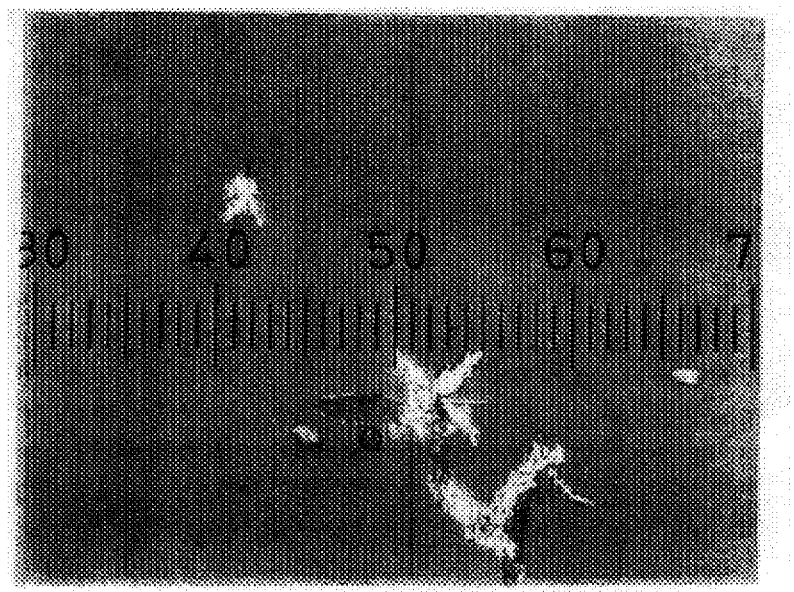
FIG. 1 depicts a microscope view of crystals in solution S1 containing 11% NaHCO$_3$ in an aqueous solution of 2% nonionic surfactant.
Figure 2:
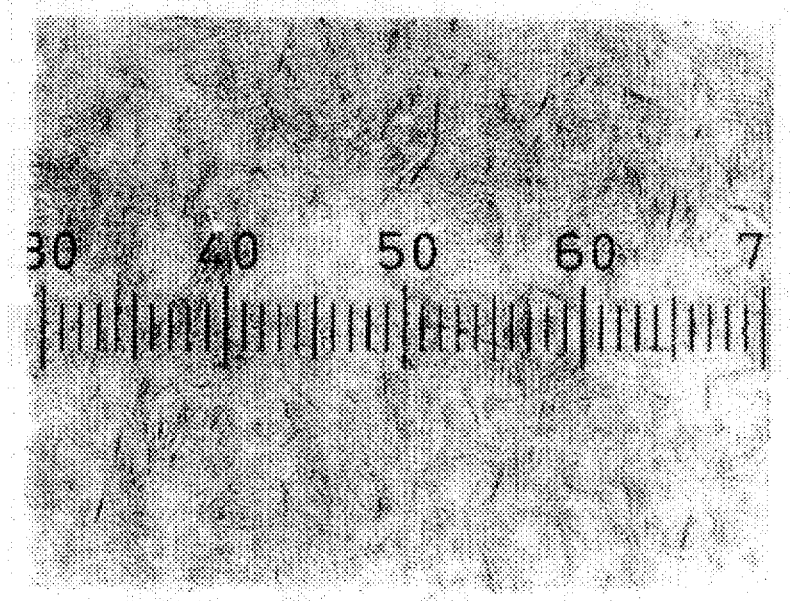
FIG. 2 depicts a microscope view of a sodium lauryl sulphate crystalline network in solution S2 containing 11% NaHCO$_3$ in an aqueous solution of 2% sodium lauryl sulphate.
Figure 3:
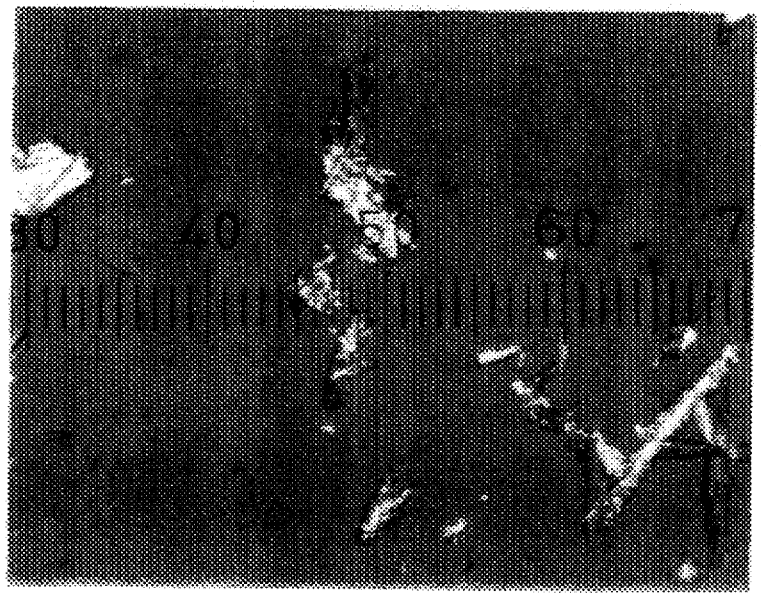
FIG. 3 depicts a microscope view of crystals in solution S3 containing 12% NaHCO$_3$ in an aqueous solution of 2% nonionic surfactant.
Figure 4:
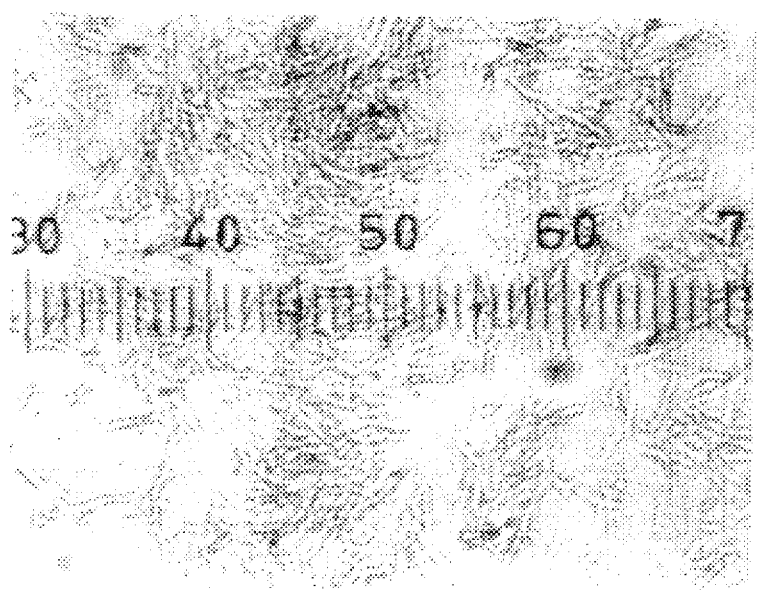
FIG. 4 depicts a microscope view of a sodium lauryl sulphate crystalline network in solution S4 containing 12% NaHCO$_3$ in an aqueous solution of 2% sodium lauryl sulphate.
Figure 5:
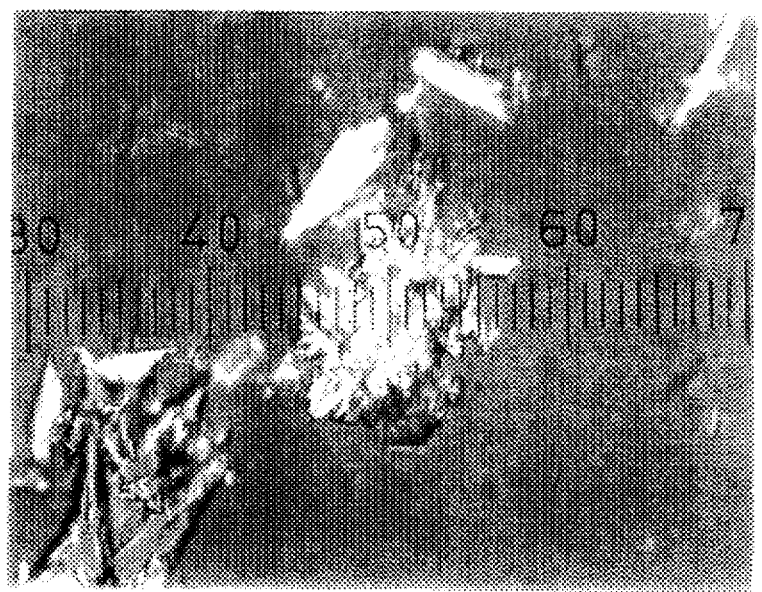
FIG. 5 depicts a microscope view of crystals in solution S5 containing 13% NaHCO$_3$ in an aqueous solution of 2% nonionic surfactant.
Figure 6:
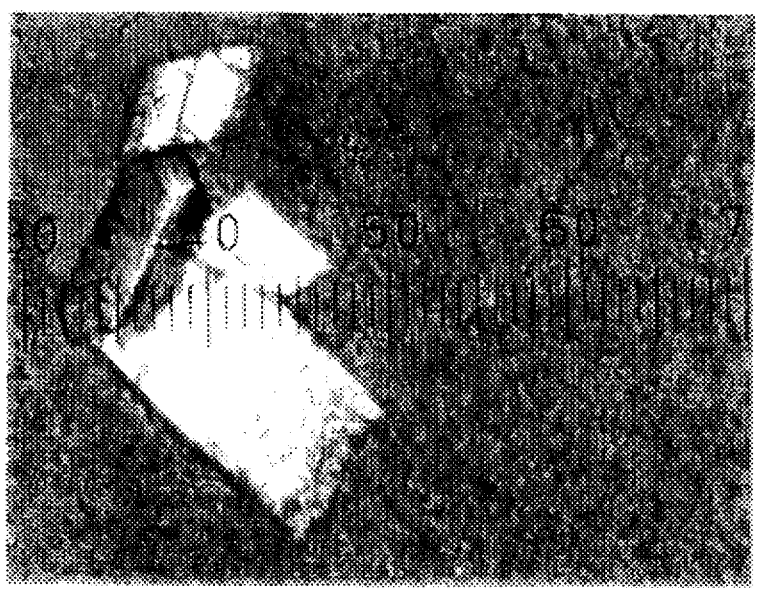
FIG. 6 depicts a microscope view of a sodium lauryl sulfate crystalline network in solution S6 containing 13% NaHCO$_3$ in an aqueous solution of 2% sodium lauryl sulphate.

The solutions S5 and S6 were supersaturated with sodium bicarbonate. In both cases, crystals were therefore observed with a microscope. The solution S1 according to the invention exhibited crystals whereas the solution S2, which constituted the prior art, did not.

Likewise, the solution S3 according to the invention exhibited crystals whereas the solution S4, which constituted the prior art, did not.

In conclusion, sodium bicarbonate was dissolved to a lesser extent in non-ionic poly(hydroxypropyl ether) surfactant medium than in sodium lauryl sulphate medium.

EXAMPLE 2

A toothpaste which was made in accordance with the invention is illustrated here.

| | |
|---|---|
| Sodium bicarbonate, Codex 0/13, sold by the company Solvay | 20 g |
| Thickening silica, sold under the name "Tixosil 333" by the company Rhone-Poulenc | 11 g |
| Sodium carboxymethylcellulose, sold under the name "Blanose 9M31F" by the company Hercules | 1.3 g |
| Sorbitol as an aqueous solution containing 70% of active material (AM) | 12.6 g AM |
| Dodecanediol polyglycerolated with 3.5 mol of glycerol | 1.5 g |
| Titanium dioxide | 0.5 g |
| Sodium fluoride | 0.33 g |
| Preservative, sweetener, fragrance | q.s. |
| Water | q.s. for 100 g |

What is claimed is:

1. A composition comprising, in an aqueous vehicle, an abrasive system containing at least one alkali metal bicarbonate and a surfactant system, wherein said surfactant system comprises at least one nonionic poly(hydroxypropyl ether) surfactant.

2. A composition according to claim 1, wherein said aqueous vehicle is a physiologically acceptable vehicle containing at least 3% by weight of water with respect to the total weight of the composition.

3. A composition according to claim 1, wherein said at least one alkali metal bicarbonate is sodium bicarbonate or potassium bicarbonate.

4. A composition according to claim 1, wherein said at least one non-ionic poly(hydroxypropyl ether) surfactant is selected from the following compounds:

(A) The compounds corresponding to the formula (I):

$$RO+C_3H_5(OH)O]_n-H \qquad (I)$$

in which the $-(C_3H_5(OH)O)-$ group is identical or different and represents the following structures (I.a), (I.b), and (I.c):

$$+CH_2-CHOH-CH_2-O+ \qquad (I.a)$$

(I.b)

(I.d)

and R and n have, together, one of the meanings a), b), or c) below:

a) R denotes a $C_{10}-C_{14}$ alkyl radical or a mixture of $C_{10}-C_{14}$ alkyl radicals, and n is a whole or decimal number from 2 to 10, b) R denotes a group of formula (II):

$$R_2-CONH-CH_2-CH_2-O-CH_2-CH_2- \qquad (II),$$

in which $R_2$ denotes a $C_{11}-C_{17}$ -alkyl or -alkenyl radical, a mixture of $C_{11}-C_{17}$ -alkyl radicals, a mixture of $C_{11}-C_{17}$ -alkenyl radicals, or a mixture of $C_{11}-C_{17}$ -alkyl radicals and $C_{11}-C_{17}$ -alkenyl radicals, and n denotes a whole or decimal number from 1 to 5, c) R denotes a group of formula (III):

$$R_3-CHOH-CH_2- \qquad (III),$$

in which $R_3$ denotes a $C_7-C_{21}$ -aliphatic, $C_7-C_{21}$ -cycloaliphatic or $C_7-C_{21}$ -arylaliphatic radical, or a mixture of any of said $C_7-C_{21}$ radicals, and n denotes a whole or decimal number from 1 to 10;

(B) the poly(hydroxypropyl ether) compounds prepared by condensation, in acid catalysis, and at a temperature ranging from 50° to 120° C., of 2 to 10 mol of glycidol per mole of either alcohol containing 10 to 14 carbon atoms or of alpha-diol containing 10 to 14 carbon atoms; and (C) the poly(hydroxypropyl ether) compounds prepared by polyaddition of glycerol monochlorohydrin to a polyhydroxylated organic compound in the presence of a strong base, with removal of water, by distillation, as said water is formed.

5. A composition according to claim 4, wherein:

a) R denotes a $C_{10}-C_{14}$ alkyl radical or a mixture of $C_{10-14}$ alkyl radicals, and n is a whole or decimal number from 3 to 6;

b) R denotes a group of said formula (II) and n denotes a whole or decimal number from 1.5 to 4;

c) R denotes a group of said formula (III), wherein the aliphatic chains denote alkyl chains which can contain from 1 to 6 ether groups, thioether groups, hydroxymethylene groups, and mixtures of any of said groups; and (B) the poly(hydroxypropyl ether) compounds prepared by condensation, in acid catalysis, and at a temperature ranging from 50° to 120° C., of 2.5 to 6 mol of glycidol per mole of either alcohol containing 10 to 14 carbon atoms or of alpha-diol containing 10 to 14 carbon atoms.

6. A composition according to claim 4, wherein said at least one non-ionic poly(hydroxypropyl ether) surfactant is selected from the following compounds:

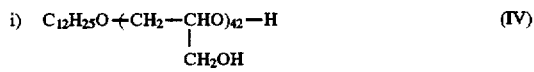
(IV)

(V)

in which formula (V), $R_1$ denotes a mixture of $C_{10}H_{21}$ and $C_{12}H_{25}$ alkyl radicals, 2i) the compounds prepared by condensation, in alkaline catalysis, of 3.5 mol of glycidol with an alpha-diol having 12 carbon atoms, 3i) the compounds of formula (VI):

$$R_2-CONH-CH_2-CH_2-O-CH_2CH_2-O-(-CH_2-CHOH-CH_2-O-)_{3.5}-H \qquad (VI)$$

in which $R_2$ denotes a mixture of radicals comprising the following alkyl and alkenyl radicals: $C_{11}H_{23}$, $C_{13}H_{27}$, the radicals derived from coconut fatty acids and the radical derived from oleic acid and 4i) the compounds prepared by condensation of 3.5 mol of glycidol with a mixture of $C_{11}$–$C_{14}$ alpha-diols.

7. A composition according to claim 4, wherein said at least one non-ionic poly(hydroxypropyl ether) surfactant is a dodecanediol polyglycerolated with 3.5 mol of glycerol.

8. A composition according to claim 1, wherein said composition is a composition for oral hygiene.

9. A composition according to claim 8, wherein said composition for oral hygiene is a dentifrice.

10. A composition according to claim 8, wherein said composition for oral hygiene is a toothpaste or tooth gel.

11. A composition according to claim 8, wherein said composition for oral hygiene is a chewing gum.

12. A composition comprising, in an aqueous vehicle, an abrasive system containing at least one alkali metal bicarbonate and a surfactant system, wherein said surfactant system consists of at least one nonionic poly(hydroxypropyl ether) surfactant.

* * * * *

UNITED STATES PATENT AND TRADEMARK OFFICE
CERTIFICATE OF CORRECTION

PATENT NO.: 5,783,172

DATED: August 12, 1998

INVENTOR(S): Jean-Marc ASCIONE et al.

It is certified that an error appears in the above-identified patent and that said Letters Patent is hereby corrected as shown below:

Claim 1, col. 5, line 56, change "(I.d)" to --(I.c)--.

Claim 6, col. 6, in Formula (IV), change "42" to --4.2--.

Signed and Sealed this

Twenty-second Day of September, 1998

Attest:

BRUCE LEHMAN

Attesting Officer

Commissioner of Patents and Trademarks